US006730641B2

(12) United States Patent
Verboom et al.

(10) Patent No.: US 6,730,641 B2
(45) Date of Patent: May 4, 2004

(54) HAIR CONDITIONING COMPOSITION

(75) Inventors: Gilles M. Verboom, Crystal Lake, IL (US); Kari L. Bauer, Oak Park, IL (US)

(73) Assignee: Alberto-Culver Company, Melrose Park, IL (US)

( * ) Notice: Subject to any disclaimer, the term of this patent is extended or adjusted under 35 U.S.C. 154(b) by 0 days.

(21) Appl. No.: 10/106,465

(22) Filed: Mar. 26, 2002

(65) Prior Publication Data

US 2003/0191035 A1 Oct. 9, 2003

(51) Int. Cl.[7] .................................................. C11D 1/62
(52) U.S. Cl. ........................ 510/119; 510/124; 510/504; 424/70.1; 424/70.28
(58) Field of Search ................................ 510/119, 124, 510/504; 424/70.1, 70.28

(56) References Cited

U.S. PATENT DOCUMENTS

| | | | | |
|---|---|---|---|---|
| 4,333,921 A | * | 6/1982 | Luedicke et al. | 424/70 |
| 4,557,928 A | | 12/1985 | Glover | |
| 4,711,775 A | * | 12/1987 | Dittmar et al. | 424/70 |
| 4,725,433 A | * | 2/1988 | Matravers | 424/70 |
| 4,765,975 A | | 8/1988 | Iovanni et al. | |
| 4,837,005 A | | 6/1989 | Brode, II et al. | |
| 4,954,335 A | | 9/1990 | Janchipraponvej | |
| 4,963,348 A | * | 10/1990 | Bolich, Jr. et al. | 424/71 |
| 4,976,956 A | | 12/1990 | Noe | |
| 5,006,331 A | * | 4/1991 | Gaskin | 424/70 |
| 5,019,377 A | * | 5/1991 | Torgerson | 424/70 |
| 5,288,483 A | * | 2/1994 | Cardin et al. | 424/70 |
| 5,306,489 A | | 4/1994 | Goldberg et al. | |
| 5,520,908 A | * | 5/1996 | Lundmark | 424/70.1 |
| 5,654,341 A | | 8/1997 | Struewing | |
| 5,925,615 A | | 7/1999 | Kern et al. | |
| 5,972,322 A | | 10/1999 | Rath et al. | |
| 5,993,792 A | | 11/1999 | Rath et al. | |
| 6,017,860 A | * | 1/2000 | Sajic et al. | 510/124 |
| 6,187,303 B1 | | 2/2001 | Ghosh et al. | |
| 6,218,346 B1 | | 4/2001 | Sajic et al. | |
| 6,221,389 B1 | | 4/2001 | Cannell et al. | |
| 6,228,352 B1 | * | 5/2001 | Leet | 424/70.16 |
| 2001/0006654 A1 | | 7/2001 | Cannell et al. | |

FOREIGN PATENT DOCUMENTS

| WO | WO 94/04125 A1 | 3/1994 |
|---|---|---|
| WO | WO 96/32921 A1 | 10/1996 |

OTHER PUBLICATIONS

Allardice et al., "Hair Conditioning Quaternary Ammonium Compounds on Various Hair Types," *Cosmetics & Toiletries*, 108, 107–109 (Mar., 1993).

* cited by examiner

*Primary Examiner*—Charles Boyer
(74) *Attorney, Agent, or Firm*—Leydig, Voit & Mayer, Ltd.

(57) ABSTRACT

The present invention provides a hair conditioning composition that comprises stearalkonium chloride and cetrimonium chloride. The hair conditioner composition of the invention preferably imparts a silky wet feel to hair and inhibits fly-away at 34% relative humidity when applied as a rinse off conditioner. In some embodiments, the hair conditioner of the invention is essentially free of an amidoamine; is characterized by a weight ratio of cetrimonium chloride to stearalkonium chloride of from about 0.65 to about 2; and/or the total combined amount of stearalkonium chloride and cetrimonium chloride is at most about 1% by weight of the composition. The present invention also provides a method of conditioning hair.

29 Claims, No Drawings

HAIR CONDITIONING COMPOSITION

FIELD OF THE INVENTION

This invention pertains to cosmetic hair conditioning compositions. In particular, the present invention relates to an aqueous hair conditioning composition that preferably imparts a silky wet feel to hair and inhibits fly-away at low relative humidity (RH) when applied as a rinse off conditioner.

BACKGROUND OF THE INVENTION

As is well known, many consumers apply a rinse-off conditioner to hair after shampooing. In this respect, hair shampoos generally contain surfactants that often leave the hair undesirably harsh, dull, and dry. In addition, shampooed hair often becomes tangled when wet and/or dry such that combing and brushing of the hair is hampered. Furthermore, especially in low humidity environments (e.g., an RH below 35% such as can be found in cold winter climates), the hair frequently exhibits poor electrostatic properties such that it is susceptible to "fly-away." Thus, to address the conditioning properties of the hair, both in the wet and dry states, conditioner is applied to render the hair more manageable, to minimize fly away, static charge, and tangling of the hair, as well as to soften hair and facilitate combing.

There is a continuing need for improved hair conditioning compositions, particularly low cost alternatives. Typically, hair conditioning formulations contain, as an active ingredient, a quaternary ammonium compound in which the molecular structure includes a nitrogen joined to four organic groups (i.e., the cation) and a negatively charged acid radical (i.e., the anion). Some quaternary ammonium compounds provide desirable antistatic properties in dry hair but suffer from poor application properties and do not provide the hair with a smooth, silky, aesthetically pleasing feel in wet hair. Other quaternary ammonium compounds provide a smooth, silky feel to wet hair and can be applied with ease, but do not provide sufficient antistatic properties to dry hair. Conventional hair conditioners often include other ingredients, such as, for example, a polyoxyethylene stearate ether like polyoxyethylene (21) stearyl ether (steareth 21) or a polyoxythylene cetearyl ether like polyexethylene (20) cetearyl ether (ceteareth 20), silicone derivates, and/or an amidoamine. Such ingredients tend to add significant cost to the end product because they are expensive raw materials.

As an example, U.S. Pat. No. 4,976,956 to Noe discloses a hair-treating composition that includes a water-soluble quaternary ammonium compound, an oil-soluble, water-dispersible quaternary ammonium compound, an acid-neutralized amidoamine compound, and a low molecular weight polydimethylsiloxane compound. According to Noe, the amidoamine is included in the hair for the purpose of imparting the hair with improved physical and cosmetic properties. However, because the amidoamine is an expensive, raw material, it adds significant manufacturing expense such that the compositions of Noe are directed to the more expensive, or premium, hair conditioning market and are ill-suited for the lower cost, or value, hair conditioning market.

Despite the availability of the foregoing approaches, it will be appreciated that there exists a need in the art for a hair conditioning composition that is relatively inexpensive, and that preferably imparts a silky wet feel to hair and inhibits fly-away at low relative humidity when applied as a rinse off conditioner. It is an object of the present invention to satisfy these needs. These and other advantages of the invention, as well as additional inventive features, will be apparent from the description of the invention provided herein.

BRIEF SUMMARY OF THE INVENTION

The present invention provides an aqueous hair conditioning composition. In accordance with the present invention, it has been found that the inventive hair conditioning composition including the blend of two particular quaternary ammonium chlorides, namely, stearalkonium chloride and cetrimonium chloride, imparts to hair a silky wet feel and inhibits fly-away at low relative humidity when applied as a rinse off conditioner. In addition, the hair conditioner of the invention preferably exhibits suitable application properties such that it can be applied readily to wet hair.

Thus, in one aspect, the present invention provides a hair conditioning composition that is essentially free of amidoamines and which comprises water, stearalkonium chloride, and cetrimonium chloride.

In another aspect, the present invention provides a hair conditioning composition that comprises cetrimonium chloride and stearalkonium chloride in a ratio (by weight) of cetrimonium chloride to stearalkonium chloride of from about 0.65 to about 2. The composition also includes water and a fatty alcohol.

In yet another aspect, the present invention provides a hair conditioning composition comprising cetrimonium chloride and stearalkonium chloride, wherein the combined amount of cetrimonium chloride and stearalkonium chloride is at most about 1% by weight of the composition. The composition also includes water and a fatty alcohol or a blend of fatty alcohols.

In still another aspect, the present invention provides a hair conditioning composition consisting essentially of from about 90 wt % to about 96 wt % water; at least about 0.25 wt % stearalkonium chloride; at least about 0.35 wt % cetrimonium chloride; from about 2.5 wt % to about 4 wt % of a fatty alcohol or a blend of fatty alcohols; from 0 wt % to about 1 wt % of a non-ionic emulsifier; from 0 wt % to about 4 wt % of a thickener; from 0 wt % to about 1 wt % of a fragrance; and from 0 wt % to about 1 wt % of a preservative.

The present invention also provides a method of conditioning hair. The method comprises applying a composition according to any aspect of the invention to the hair, and rinsing the hair with water.

The combination of cetrimonium chloride and stearalkonium chloride, in accordance with the present invention, provides the hair conditioning composition with improved conditioning properties, without requiring expensive additives such as an amidoamine and/or an ethoxylated emulsifier, such as a polyoxyethylene glycol ether of stearyl alcohol (e.g., steareth 21) or a polyoxthylene glycol ether of cetearyl alcohol (e.g., ceteareth 20), which are commonly found in conventional hair conditioners. As such, if desired, the present invention advantageously can allow for providing a less expensive alternative to many premium products that include such expensive raw materials. Furthermore, the cetrimonium chloride and stearalkonium chloride surprisingly can be present in relatively small combined quantities (e.g., 1% by weight of the composition or less) while still providing the desired conditioning properties, thereby further reducing the manufacturing cost and, therefore, the cost passed on to the consumer.

The present invention may be best understood with reference to the following detailed description of the preferred embodiments.

DETAILED DESCRIPTION OF THE INVENTION

The present invention is predicated, at least in part, on the surprising and unexpected discovery that a hair conditioning composition comprising a particular combination of quaternary ammonium compounds, that is, cetrimonium chloride and stearalkonium chloride, exhibits improved conditioning properties. In this respect, the combination of cetrimonium chloride and stearalkonium chloride synergistically confers improved conditioning properties to hair such as, for example, ease of application, silky wet feel, and inhibition of fly-away at low relative humidity (e.g. as low as 34%).

The hair conditioner according to the invention can be used as a rinse off conditioner or a leave-in conditioner, but in preferred embodiments, takes the form of a rinse off conditioner.

Because of the improved conditioning properties exhibited by the combination of cetrimonium chloride and stearalkonium chloride, pursuant to the present invention, other conditioning additives are not required and can be excluded, if desired. For example, in some embodiments, the inventive hair conditioning composition is essentially free (e.g., less than about 0.1% by weight and preferably entirely absent) of an amidoamine. In addition or as an alternative to being free of an amidoamine, some embodiments of the inventive hair conditioner composition are essentially free of a silicone derivatives (e.g., oils such as dimethicone, cyclomethicone, dimethicone co-polyol derivatives or the like) or an ethoxylated emulsifier such as, for example, a polyoxyethylene stearate ether (e.g., steareth 21), or polyoxethylene cetearyl ether (e.g., ceteareth 20) or the like. In this respect, although some non-ionic emulsifiers can be included in the inventive hair conditioning composition, ethoxylated non-ionic emulsifiers are preferably absent. By "essentially free" of the silicone derivative or ethoxylated non-ionic emulsifier, it is meant that the silicone derivatives or ethoxylated non-ionic emulsifiers preferably are totally absent but that they can be present in small amounts (e.g., less than about 0.01%) so that they do not measurably impact the conditioning properties of the composition.

Surprisingly, it has been found, in accordance with the present invention, that the synergistic combination of cetrimonium chloride and stearalkonium chloride permits the use of less total quantities of the quaternary ammonium compounds. Any suitable amount of cetrimonium chloride and stearalkonium chloride can be used in accordance with the invention. However, in some embodiments, for example, in order to reduce manufacturing cost, the hair conditioner composition includes 1% (by weight) or less of the combined amount of cetrimonium chloride and stearalkonium chloride. For example, in some embodiments, the hair conditioner includes 0.9% or less of the total amount of cetrimonium chloride and stearalkonium chloride; sometimes, 0.8% or less of the total amount of cetrimonium chloride and stearalkonium chloride.

Thus, the cetrimonium chloride and stearalkonium chloride in combination are active conditioning ingredients in the inventive hair conditioning composition, and in preferred embodiments, they are the only active conditioning ingredients. The cetrimonium chloride and stearalkonium chloride can be provided in any suitable weight ratio relative to each other. In some embodiments, the ratio by weight of cetrimonium chloride to stearalkonium chloride is from about 0.65 to about 2.

Stearalkonium chloride ($C_{27}H_{50}NCl$) is an oil soluble, water dispersible quaternary ammonium chloride having the formula:

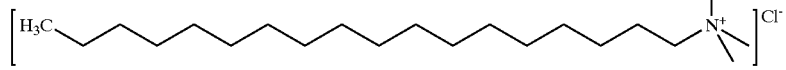

The stearalkonium chloride can be present in any suitable amount. Preferably, the stearalkonium chloride is present in the composition in an amount of at least about 0.25% by weight of the composition. In preferred embodiments, the amount of stearalkonium chloride is limited so as to reduce manufacturing and end product costs. Thus, preferably, the amount of stearalkonium chloride is from about 0.25% to about 1% by weight of the composition. Even more preferably, the total amount of stearalkonium chloride and cetrimonium chloride is at most about 1% by weight of the composition, such that the amount of the stearalkonium chloride is from about 0.25% to about 0.65% by weight of the composition.

Cetrimonium chloride ($C_{19}H_{42}ClN$) is a water soluble quaternary ammonium chloride having the formula:

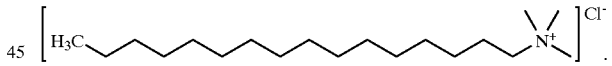

The cetrimonium chloride can be present in any suitable amount. Preferably, the cetrimonium chloride is present in an amount of at least about 0.35% by weight of the composition. In preferred embodiments, the amount of cetrimonium chloride is limited so as to reduce manufacturing and end product costs. Thus, preferably, the amount of cetrimonium chloride is from about 0.35% to about 1% by weight of the composition. Even more preferably, the total amount of stearalkonium chloride and cetrimonium chloride is at most about 1% by weight of the composition, such that the amount of the stearalkonium chloride is from about 0.35% to about 0.75% by weight of the composition.

It is to be noted that the ranges set forth herein are calculated with respect to a 100% active concentration of the ingredients. As a result, if, for example, the stearalkonium chloride or the cetrimonium chloride is provided in a form in which the stearalkonium chloride or cetrimonium chloride is present only in a concentration of, for example, 25%, then, of course, it is desirable to use 4 times the amount of the form to achieve the desired amount of the stearalkonium chloride or cetrimonium chloride in the composition.

The inventive hair conditioning composition is aqueous. In this respect, the amount of water (diluent) in the composition can be any suitable amount, e.g., from about 70% to about 98% by weight of the composition, preferably from about 90% to about 96% by weight of the composition, even more preferably, from about 93% to about 95% by weight of the composition.

Although not essential, at least one preservative in any effective amount is useful in preferred hair conditioning compositions of the invention. For example, the preservative can be selected to kill bacteria that might otherwise be sustained or multiply in the composition. Such preservatives are well known to those of ordinary skill in the art and examples of suitable preservatives will thus be readily be apparent to those of ordinary skill in the art.

Examples of suitable preservatives include disodium EDTA, trisodium EDTA, trisodium EDTA, tetrasodium EDTA, isothiazolinones (e.g., KATHON CG, commercially available from Rohm & Haas), DMDM hydantoin, and combinations thereof. As will be appreciated by one of ordinary skill in the art, DMDM hydantoin is understood worldwide pursuant to the nomenclature for cosmetic products set forth in the International Cosmetic Ingredient Directory and Handbook. The chemical name for DMDM hydantoin is 1,3-dimethylol-5,5-dimethyl hydantoin, which is commercially available from Lonza, Inc. of Fairlawn, N.J. under the trade name "Glydant." In one embodiment, the preservative includes disodium EDTA and DMDM hydantoin in combination. Preferably, the preservative is provided in an amount of from about 0.02% to about 1% by weight of the composition, more preferably, from about 0.1% to about 1% by weight of the composition, even more preferably, from about 0.1% to about 0.5% by weight of the composition, and still more preferably, from about 0.2% to about 0.3% by weight of the composition.

The inventive hair conditioning composition can also include, optionally, at least one thickener, if desired. The thickener, if used, enhances the viscosity of the hair conditioning composition and facilitates combing, especially with wet hair. The thickener can be, for example, in the form of any of a number of suitable alcohols, such as fatty alcohols, as will be appreciated readily by one of ordinary skill in the art. Especially suitable thickeners include, but are not limited to, stearyl alcohol, cetyl alcohol, behenyl alcohol, and combinations thereof. The thickener is desirably present in the composition in an amount ranging from about 0.5% to about 11% by weight, more preferably from about 1% to about 5% by weight, and even more preferably from about 2% to about 4% by weight of the composition, and still more preferably, from about 2.5% to about 4% by weight of the composition. In preferred embodiments, the thickener includes both stearyl alcohol and cetyl alcohol. In these embodiments, the amount of each of the stearyl alcohol and cetyl alcohol is preferably from about 0.5% to about 5% by weight, more preferably, from about 1% to about 2.5% by weight, and even more preferably from about 1.2% to about 1.8% by weight of the composition.

Other optional ingredients that may be useful in the hair conditioning compositions of the present invention include opacifiers, hair strengtheners, fragrances, and/or dyes. An opacifier is not necessary for the function of the hair conditioner composition but can impart an enhanced appearance such that the hair conditioning composition looks rich and creamy and not translucent. Examples of suitable opacifiers (as will be appreciated by one of ordinary skill in the art) include, but are not limited to, a glyceryl stearate, including any of a number of glyceryl monostearates, especially the glyceryl monostearate of the formula $C_{21}H_{42}O_4$, which is commercially available from Lonza, Inc. of Fairlawn, N.J. However, the glyceryl monostearate can be in other forms including the self-emulsified form (identified in the art as "SE") containing sodium and/or potassium stearate. The opacifier (e.g., glyceryl monostearate) is desirably included in the composition in an amount ranging from about 0.1 to about 2% by weight of the composition, preferably from about 0.15% to about 10% by weight of the composition, even more preferably from about 0.15% to about 0.4% by weight of the composition, and still more preferably about 0.25% by weight of the composition.

The hair conditioner composition of the present invention can have any suitable pH and viscosity. Preferably, the inventive composition exhibits a pH of from about 3 to about 6.5, more preferably from about 3 to about 5. To achieve a desired pH, suitable acids can be optionally included, if desired, as will be apparent to those skilled in the art. By way of example, preferred acids include, but are not limited to, citric acid, lactic acid, glycolic acid and the like. Citric acid is a preferred acid.

The viscosity of the composition of the present invention preferably ranges from about 1,000 cps to about 20,000 cps, more preferably from about 2,000 cps to about 10,000 cps. It is noteworthy that the viscosity of the composition can be determined in bulk and/or as packaged (e.g., as a finished good). In particular, the conditioner composition is made in a large quantity mixing tank, typically in 2,000 gallon batches. Once a batch is made in bulk, the viscosity is typically measured. Preferably, the composition has a viscosity in bulk of from about 1,000 cps to about 4,500 cps, and more preferably from about 1,500 cps to about 3,500 cps.

The bulk conditioner having the desired viscosity is then pumped, subjected to screens, and then the final product is prepared by forcing the conditioner through a nozzle in order to fill the finished goods package. During this filling process, the viscosity of the conditioner composition typically increases. Preferably, after packaging, the conditioner has a viscosity of from about 2,000 cps to about 8,000 cps, preferably from about 3,500 cps to about 6,000 cps.

The following examples further illustrate the invention but should not be construed as in any way limiting its scope.

EXAMPLE 1

This example demonstrates methods for producing exemplary hair conditioning compositions of the invention.

The list of ingredients and their wt. % amounts for each of Hair Conditioning Compositions 1A, 1B, and 1C are summarized in Table 1. The preparation of Hair Conditioning Composition 1A consisted of a two-part process. Deionized water, citric acid, and disodium EDTA were placed in an appropriately sized vessel and heated, with stirring, to 80° C. In a separate vessel, cetyl alcohol, stearyl alcohol, glyceryl stearate, and stearalkonium chloride (85% active) ("oil-phase ingredients") were melted together with stirring to form a homogeneous mixture. The oil phase ingredient mixture was added to the aqueous mixture and stirred for 10 minutes at 80° C. The mixture was then cooled to 60° C. and cetrimonium chloride (25% active) was added under slow mixing. The mixture was then further cooled to 45° C. and DMDM hydantoin and the fragrance were added. Hair Conditioning Composition 1A had a final pH of 3.31

Hair Conditioning Compositions 1B and 1C were prepared using a one-part process. Deionized water, citric acid, and disodium EDTA were placed in an appropriately sized vessel and heated, with stirring, to 80° C. When the aqueous solution had reached 70° C., cetyl alcohol, stearyl alcohol, glyceryl stearate (if present), and stearalkonium chloride (85% active) were added. The mixture was heated with stirring until the temperature reached 80° C. and then the temperature was maintained for 10 minutes. The mixture was then cooled to 60° C. and cetrimonium chloride (25% active) was added at a slow mixing speed. The mixture was then cooled to 45° C. and DMDM hydantoin and the fragrance were added. Hair Conditioning Compositions 1B and 1C had a final pH of 3.44 and 3.37, respectively. As used herein, the "total amount of actives" refers to the total amount of cetrimonium chloride and stearalkonium chloride in the formulation.

TABLE 1

| Hair Conditioning Composition | 1A (wt. %) | 1B (wt. %) | 1C (wt. %) |
| --- | --- | --- | --- |
| Water | 93.98 | 94.16 | 94.36 |
| Citric Acid | 0.015 | 0.015 | 0.015 |
| Cetyl Alcohol | 1.20 | 1.80 | 1.80 |
| Stearyl Alcohol | 1.80 | 1.20 | 1.20 |
| Cetrimonium Chloride, 25% | 1.70 | 1.44 | 1.44 |
| Stearalkonium Chloride, 85% | 0.56 | 0.64 | 0.64 |
| Glyceryl Stearate | 0.20 | 0.20 | 0 |
| DMDM Hydantoin | 0.20 | 0.20 | 0.20 |
| Disodium EDTA | 0.03 | 0.03 | 0.03 |
| Fragrance | 0.315 | 0.315 | 0.315 |
| Total Amount of Actives | 0.90 | 0.90 | 0.90 |

EXAMPLE 2 (COMPARATIVE EXAMPLE)

This example demonstrates methods for producing comparative hair conditioning compositions containing only stearalkonium chloride.

The list of ingredients and their wt. % amounts for each of Comparative Hair Conditioning Compositions 2A, 2B, and 2C are summarized in Table 2. The preparation of Hair Conditioning Composition 2A consisted of a two-part process. Deionized water, citric acid, and disodium EDTA were placed in an appropriately sized vessel and heated, with stirring, to 80° C. In a separate vessel, cetyl alcohol, stearyl alcohol, and stearalkonium chloride (85% active) ("oil-phase ingredients") were melted together with stirring to form a homogeneous mixture. The oil phase ingredient mixture was added to the aqueous mixture and stirred for 10 minutes at 80° C. The mixture was then cooled to 45° C. and DMDM hydantoin was added. Hair Conditioning Composition 2A had a final pH of 3.10.

Hair Conditioning Compositions 2B and 2C were prepared using a one-part process. Deionized water, citric acid, and disodium EDTA were placed in an appropriately sized vessel and heated, with stirring, to 80° C. When the aqueous solution had reached 70° C., cetyl alcohol, stearyl alcohol, glyceryl stearate (if present), and stearalkonium chloride (85% active) were added. The mixture was heated with stirring until the temperature reached 80° C. and then the temperature was maintained for 10 minutes. The mixture was then cooled to 45° C. and DMDM hydantoin and fragrance were added. Hair Conditioning Compositions 2B and 2C had a final pH of 3.13 and 3.38, respectively.

TABLE 2

| Hair Conditioning Composition | 2A (wt. %) | 2B (wt. %) | 2C (wt. %) |
| --- | --- | --- | --- |
| Water | 95.54 | 95.17 | 95.38 |
| Citric Acid | 0.03 | 0.025 | 0.015 |
| Cetyl Alcohol | 1.80 | 1.80 | 1.80 |
| Steayl Alcohol | 1.20 | 1.20 | 1.20 |
| Stearalkonium Chloride, 85% | 1.10 | 1.06 | 1.06 |
| Glyceryl Stearate | 0 | 0.20 | 0 |
| DMDM Hydantoin | 0.30 | 0.20 | 0.20 |
| Disodium EDTA | 0.03 | 0.03 | 0.03 |
| Fragrance | 0 | 0.315 | 0.315 |
| Total Amount of Actives | 0.94 | 0.90 | 0.90 |

EXAMPLE 3 (COMPARATIVE EXAMPLE)

This example demonstrates methods for producing comparative hair conditioning compositions containing only cetrimonium chloride.

The list of ingredients and their wt. % amounts for each of the comparative Hair Conditioning Compositions 3A, 3B, 3C, and 3D are summarized in Table 3. The preparation of Hair Conditioning Composition 3A consisted of a two-part process. Deionized water, citric acid, disodium EDTA, and cetrimonium chloride (25%) were placed in an appropriately sized vessel and heated, with stirring, to 80° C. In a separate vessel, cetyl alcohol and stearyl alcohol ("oil-phase ingredients") were melted together with stirring to form a homogeneous mixture. The oil phase ingredient mixture was added to the aqueous mixture and stirred for 10 minutes at 80° C. The mixture was then cooled to 45° C. and DMDM hydantoin was added. Hair Conditioning Composition 3A had a final pH of 3.21.

The preparation of Hair Conditioning Composition 3B was similar to that for Hair Conditioning Composition 3A, except that the 25% cetrimonium chloride was added in two portions. Deionized water, citric acid, disodium EDTA, and half the total amount of cetrimonium chloride (25%) were placed in an appropriately sized vessel and heated, with stirring, to 80° C. In a separate vessel, cetyl alcohol, stearyl alcohol, and glyceryl stearate ("oil-phase ingredients") were melted together with stirring to form a homogeneous mixture. The oil phase ingredient mixture was added to the aqueous mixture and stirred for 10 minutes at 80° C. The mixture was then cooled to 60° C. and the remainder of the cetrimonium chloride (25%) was added. The mixture was then cooled to 45° C. and DMDM hydantoin was added. Hair Conditioning Composition 3B had a final pH of 3.29.

Hair Conditioning Compositions 3C and 3D were prepared using a one-part process. Deionized water, citric acid, and disodium EDTA were placed in an appropriately sized vessel and heated, with stirring, to 80° C. When the aqueous solution had reached 70° C., cetyl alcohol, stearyl alcohol, and glyceryl stearate (if present) were added. The mixture was heated with stirring until the temperature reached 80° C. and then the temperature was maintained for 10 minutes. The mixture was then cooled to 60° C. and cetrimonium chloride (25%) was added. The mixture was then cooled to 40° C. and DMDM hydantoin and fragrance were added. Hair Conditioning Compositions 3C and 3D had a final pH of 3.17 and 3.4, respectively.

TABLE 3

| Hair Conditioning Composition | 3A (wt. %) | 3B (wt. %) | 3C (wt. %) | 3D (wt. %) |
|---|---|---|---|---|
| Water | 93.34 | 93.14 | 92.61 | 92.82 |
| Citric Acid | 0.03 | 0.03 | 0.025 | 0.015 |
| Cetyl Alcohol | 1.80 | 1.20 | 1.80 | 1.80 |
| Stearyl Alcohol | 1.20 | 1.80 | 1.20 | 1.20 |
| Cetrimonium Chloride, 25% | 3.40 | 3.40 | 3.620 | 3.62 |
| Glyceryl Stearate | 0 | 0.20 | 0.20 | 0 |
| DMDM Hydantoin | 0.20 | 0.20 | 0.20 | 0.20 |
| Disodium EDTA | 0.03 | 0.03 | 0.03 | 0.03 |
| Fragrance | 0 | 0 | 0.315 | 0.315 |
| Total Amount of Actives | 0.85 | 0.85 | 0.91 | 0.91 |

EXAMPLE 4

The following example illustrates the improved properties of conditioning compositions comprising cetrimonium chloride with respect to the feel of hair conditioning compositions during application, after application while wet, and when dry as well as the ease of combing when wet.

The comparative and inventive Hair Conditioning Compositions of Examples 1, 2, and 3 (1A-1C, 2A-2C, and 3A-3D) were evaluated with respect to feel and drag during combing using four tests. Each Hair Conditioning Composition was evaluated using similar bleached tresses of hair (obtained from International Hair Importers) that were pre-washed with VO5 brand shampoo, commercially available from Alberto Culver, and rinsed thoroughly with tap water having a temperature of 40±1.5 C. A comb having a wide-toothed end and a fine-toothed end was used to evaluate the comb drag. The comb was pre-washed by dipping 5 times in 1:20 VO5 Normal Shampoo:water and rinsed for 30 seconds under flowing tap water.

A pre-washed tress was rinsed for 15 seconds under flowing tap water and then 1.5 mL VO5 Normal Shampoo was applied to the tress and lathered for 30 seconds. The tress was rinsed for 30 seconds under flowing tap water while stroking the tress to ensure complete removal of the shampoo. Then, 1.5 mnL of one of Hair Conditioning Composition 1A-1C, 2A-2C, or 3A-3D was applied to the tress and the tress was massaged for 30 seconds. The feel of the hair tress with conditioner on the fingers during massaging was evaluated for slickness, lubricity, and richness ("Application Feel Test").

The tress was then rinsed for 30 seconds under flowing tap water while stroking with the fingers to ensure complete removal of the conditioner from the tress. After removal of the conditioner, the feel of the wet tress on the fingers was evaluated for slipperiness and coarseness of the hair texture and the appearance of the hair under the water flow ("Wet Feel Test").

The excess water was wrung from the tress and the tress was placed onto a tress rack. The wet tress was detangled once using the wide-toothed end of the pre-washed comb and the amount of drag encountered was recorded. The tress was combed three times using the fine-toothed end of the pre-washed comb and the amount of drag encountered was again recorded. The drag of the comb against the hair ("Wet Comb Test") was rated as described below. The tress was allowed to dry in air until dry to the touch (dried overnight). The dried tress was combed three times with the fine-toothed end of the pre-washed comb. The feel of the dry hair ("Dry Feel Test") was evaluated for softness and smoothness. The procedure was then repeated for each of the Hair Conditioning Compositions.

The results of the application feel test, wet feel test, wet comb test, and dry feel test for each of the Hair Conditioning Compositions 1A-1C, 2A-2C, and 3A-3D are summarized in Table 4.

TABLE 4

| Hair Conditioning Composition | Application Feel | Wet Feel | Wet Comb | Dry Feel |
|---|---|---|---|---|
| 1A (invention) | Easy - feels rich and slick | Soft and silky | Very slight drag - soft, smooth, easy to detangle | Soft and silky |
| 1B (invention) | Easy - feels rich and slick | Soft and silky | Very slight drag - soft, smooth, easy to detangle | Soft and silky |
| 1C (invention) | Easy - feels rich and slick | Soft and silky | Very slight drag - soft, smooth, easy to detangle | Soft and silky |
| 2A (Comparative) | Difficult - quick absorption | Very slick | Slight drag - fairly easy to detangle but lacks silky feel | No data collected |
| 2B (Comparative) | Difficult - hair feels rough | Rough - feeling of drag | Slight drag - fairly easy to detangle but lacks silky feel | Soft and silky |
| 2C (Comparative) | Difficult - hair feels rough | Rough - feeling of drag | Slight drag - fairly easy to detangle but lacks silky feel | Soft and silky |
| 3A (Comparative) | Easy - feels rich and slick | Soft and silky | Very slight drag - soft, smooth, easy to detangle | Soft and silky |
| 3B (Comparative) | Easy - feels rich and slick | Soft and silky | Very slight drag - soft, smooth, easy to detangle | Soft and silky |

TABLE 4-continued

| Hair Conditioning Composition | Application Feel | Wet Feel | Wet Comb | Dry Feel |
|---|---|---|---|---|
| 3C (Comparative) | Easy - feels rich and slick | Soft and silky | Very slight drag - soft, smooth, easy to detangle | Soft and silky |
| 3D (Comparative) | Easy - feels rich and slick | Soft and silky | Very slight drag - soft, smooth, easy to detangle | Soft and silky |

With respect to terminology, as used herein, the term "severe drag" indicates uncombability such that the comb will not pass through tress without extreme force. The term "heavy drag" indicates that the comb will pass, but only with some snagging or catching, and that the tress feels very rough against comb. The term "moderate drag" indicates that the comb will pass through without snagging, but that the tress feels rough and that rasping sound and friction are evident. The term "slight drag," indicates that the tress combs easily, but some dragging is readily perceived. The term "very slight drag" indicates that the comb glides through the tress with some friction barely perceived. The term "no drag" indicates that the comb passes through the tress with no apparent friction.

The results in Table 4 show that hair tresses treated with Hair Conditioning Compositions 1A-1C of the invention and comparative Hair Conditioning Compositions 3A-3D comprising cetrimonium chloride have superior properties to the comparative Hair Conditioning Compositions 2A-2C, without cetrimonium chloride, with respect to the feel of the hair during application, while wet, the combability of the hair while wet, and the feel of the dry hair.

EXAMPLE 5

The following example illustrates the improved properties of conditioning compositions comprising stearalkonium chloride with respect to the static properties of the dry hair.

Each of the dried tresses from Example 4, having been washed and conditioned with one of the comparative or inventive Hair Conditioning Compositions of Examples 1,2 and 3 (1A-1C, 2A-2C, and 3A-3D), were evaluated with respect to the presence of electrostatic charge ("static flyaway") at low humidity (34% RH, 71° C.) and high humidity (60% RH, 71° C.). The static flyaway test was conducted using a dry plastic comb (Sally Beauty Supply).

The tresses from Example 4 were hung on a tress rack in ambient temperature (71° C.) and ambient relative humidity (60%). The tresses were combed 10 times vigorously with the fine-toothed end of the comb. The comb was then placed close to the tress without touching and the tress was observed to see if any of the hair strands were attracted to the comb indicating the presence of static flyaway. The observation of static flyaway was recorded for each of the tresses.

The tresses were then evaluated for static flyaway in a low humidity environment. The low humidity environment was established either in the lab or by placing a shallow dish containing a thin layer of dessicant (98% calcium chloride hexanhydrate, Aldrich) inside an airtight chamber. The chamber was allowed to equilibrate and the relative humidity was adjusted to approximately 30% through addition of more dessicant. The relative humidity and temperature were measured using a hygrometer/thermometer (Fisher Scientific). Each of the dried hair tresses from Example 4 were placed inside the airtight chamber. The airtight chamber containing the tresses was allowed to equilibrate for 24 hours while maintaining a relative humidity of approximately 30%. The final relative humidity was 34% and the final temperature was 71° C. The tresses were then removed from the airtight chamber and were combed 10 times vigorously with the fine-toothed end of a comb. The comb was then placed close to the tress without touching and the tress was observed to see if any of the hair strands were attracted to the comb indicating the presence of static flyaway. The observation of static flyaway was recorded for each of the tresses. The results of the static flyaway experiment are summarized in Table 5.

TABLE 5

| Hair Conditioning Composition | Static Flyaway 60% RH, 71° C. | Static Flyaway 34% RH, 71° C. |
|---|---|---|
| 1A (invention) | No | No |
| 1B (invention) | No | No |
| 1C (invention) | No | No |
| 2A (Comparative) | No data collected | No data collected |
| 2B (Comparative) | No | No |
| 2C (Comparative) | No | No |
| 3A (Comparative) | Yes | Yes |
| 3B (Comparative) | No data collected | No data collected |
| 3C (Comparative) | Yes | Yes |
| 3D (Comparative) | Yes | Yes |

The results in Table 5 show that hair tresses treated with Hair Conditioning Compositions 1A-1C of the invention and comparative Hair Conditioning Compositions 2A-2C comprising stearalkonium chloride do not produce static flyaway unlike the comparative Hair Conditioning Compositions 3A-3D, which contain only cetrimonium chloride.

EXAMPLE 6

The following example illustrates the wet feel and static flyaway properties of hair conditioning compositions of the invention containing different relative ratios of stearalkonium chloride and cetrimonium chloride.

A series of hair conditioning compositions were prepared containing different relative amounts of stearalkonium chloride (85% active) and cetrimonium chloride (25% active). Hair Conditioning Compositions 6A-6E each contained a dye (0.001%), 0.015 wt. % citric acid, 0.030 wt. % disodium EDTA, 1.800 wt. % cetyl alcohol, 1.200 wt. % stearyl alcohol, 0.200 wt. % glyceryl stearate, 0.200 wt. % DMDM hydantoin, 0.350 wt. % fragrance, 0.900 wt. % total active ingredients (stearalkonium chloride, cetrimonium chloride), and a balance of water (qs). Hair Conditioning Compositions 6F and 6G contained the same ingredients as Hair Conditioning Compositions 6A-6E except that they contained only 0.800 wt. % total active ingredients (stearalkonium chloride, cetrimonium chloride). The relative ratio of stearalkonium chloride to cetrimonium chloride was 0.66, 8, 3.5, 0.5, 0.286, 3, and 0.6 for Hair Conditioning Compositions 6A, 6B, 6C, 6D, 6E, 6F, and 6G, respectively. The resulting conditioning compositions were evaluated for wet application feel using the procedure described in Example 4 and for static flyaway using the procedure described in Example 5. The relative amounts of stearalkonium chloride and cetrimonium chloride as well as the results of the wet application feel test and static flyaway test for each of the Hair Conditioning Compositions 6A-6G are summarized in Table 6.

TABLE 6

| Ingredients | 6A | 6B | 6C | 6D | 6E | 6F | 6G |
|---|---|---|---|---|---|---|---|
| Stearalkonium chloride (% active amount) | 0.544 | 0.100 | 0.200 | 0.600 | 0.700 | 0.200 | 0.500 |
| Cetrimonium chloride (% active amount) | 0.360 | 0.800 | 0.700 | 0.300 | 0.200 | 0.600 | 0.300 |
| Total active ingredients (%) | 0.904 | 0.900 | 0.900 | 0.900 | 0.900 | 0.800 | 0.800 |
| Ratio cetrimonium chloride to stearalkonium chloride | 0.66 | 8 | 3.5 | 0.5 | 0.286 | 3 | 0.6 |
| Application Feel (Wet Test) | Good | Fair | Fair | Poor | Poor | Good | Poor |
| Static Flyaway (33% RH) | No | Very Much | Some | No | No | Slight | No |

The results shown in Table 6 demonstrate that a relative ratio of cetrimonium chloride to stearalkonium chloride of about 0.65 to about 2 provides optimal results from both the application feel test and static flyaway test.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

What is claimed is:

1. A hair conditioning composition consisting essentially of water, stearalkonium chloride, cetrimonium chloride, cetyl alcohol, and stearyl alcohol, wherein the stearalkonium chloride and cetrimonium chloride are present in a combined amount of at most 1% by weight of the composition.

2. The hair conditioning composition of claim 1, comprising at least one of the following additives: a thickener, a dye, a fragrance, and/or a preservative.

3. The hair conditioning composition of claim 1, wherein the composition imparts a silky wet feel to hair when applied as a rinse off conditioner and inhibits fly-away at 34% relative humidity when applied as a rinse off conditioner.

4. The hair conditioning composition of claim 1, wherein the composition is essentially free of an ethoxylated emulsifier.

5. The hair conditioning composition of claim 1, wherein the ratio by weight of cetrimonium chloride to stearalkonium chloride is from about 0.6 to about 2.

6. A hair conditioning composition comprising water, a fatty alcohol, stearalkonium chloride, and cetrimonium chloride, wherein (a) the ratio by weight of cetrimonium chloride to stearalkonium chloride is from about 0.6 to about 2, (b), wherein the stearalkonium chloride and cetrimonium chloride are present in a combined amount of at most 1% by weight of the composition, and (c) the stearalkonium chloride and cetrimonium chloride are the only active conditioning ingredients present in the composition.

7. The hair conditioning composition of claim 6, wherein the composition imparts a silky wet feel to hair when applied as a rinse off conditioner and inhibits fly-away at 34% relative humidity when applied as a rinse off conditioner.

8. The hair conditioning composition of claim 6, wherein the composition is essentially free of an amidoamine.

9. The hair conditioning composition of claim 6, wherein the cetrimonium chloride is present in an amount of at least about 0.35% by weight of the composition.

10. The hair conditioning composition of claim 6, wherein the stearalkonium chloride is present in an amount of at least about 0.25% by weight of the composition.

11. The hair conditioning composition of claim 6, wherein the fatty alcohol is present in an amount of from about 2.5% to about 4% by weight of the composition.

12. The hair conditioning composition of claim 6, wherein the water is present in an amount of from about 90% to about 96% by weight of the composition.

13. The hair conditioning composition of claim 6, further comprising at least one of the following additives: a thickener, a dye, a fragrance, and/or a preservative.

14. The hair conditioning composition of claim 13, wherein the preservative is present in an amount of from about 0.02% to about 1% by weight of the composition and is selected from the group consisting of 1,3-dimethylol-5, 5-dimethyl hydantoin, disodium EDTA, trisodium EDTA, tetrasodium EDTA, isothiazolinones, and combinations thereof.

15. The hair conditioning composition of claim 13, wherein the thickener is present in an amount of from about 2% to about 4% by weight of the composition and is selected from the group consisting of stearyl alcohol, cetyl alcohol, behenyl alcohol, and combinations thereof.

16. The hair conditioning composition of claim 6, wherein the pH of the composition is from about 3.1 to about 5.

17. The hair conditioning composition of claim 6, wherein the viscosity of the composition is from about 2,000 cps to about 10,000 cps.

18. A hair conditioning composition that is essentially free of an ethoxylated emulsifier, the composition comprising about 90 wt % to about 96 wt % water, a fatty alcohol, cetrimonium chloride, and stearalkonium chloride, wherein the stearalkonium chloride and cetrimonium chloride are present in a combined amount of at most about 1% by weight of the composition.

19. The hair conditioning composition of claim 18, wherein the composition imparts a silky wet feel to hair when applied as a rinse off conditioner and inhibits fly-away at 34% relative humidity when applied as a rinse off conditioner.

20. The hair conditioning composition of claim 18, further comprising a non-ionic emulsifier.

21. The hair conditioning composition of claim 18, wherein the composition is essentially free of an amidoamine.

22. The hair conditioning composition of claim 18, wherein the fatty alcohol is present in an amount of from about 2.5% to about 4% by weight of the composition.

23. The hair conditioning composition of claim 18, further comprising at least one of the following additives: a thickener, a dye, a fragrance, and/or a preservative.

24. A hair conditioning composition consisting essentially of from about 90 wt % to about 96 wt % water, at least about 0.25 wt % stearalkonium chloride, at least about 0.35 wt % cetrimonium chloride, from about 2.5 wt % to about 4 wt % of a blend of fatty alcohols, from 0 wt % to about 1 wt % of a non-ionic emulsifier, from 0 wt % to about 4 wt % of a thickener, from 0 wt % to about 1 wt % of a fragrance, and from 0 wt % to about 1 wt % of a preservative, wherein the stearalkonium chloride and stearalkonium chloride are present is a combined amount of at most 1% by weight of the composition.

25. The hair conditioning composition of claim 24, wherein the composition is essentially free of an amidoamine.

26. A method of conditioning hair comprising applying the composition of claim 1 to the hair, and rinsing the hair with water.

27. A method of conditioning hair comprising applying the composition of claim 6 to the hair, and rinsing the hair with water.

28. A method of conditioning hair comprising applying the composition of claim 18 to the hair, and rinsing the hair with water.

29. A method of conditioning hair comprising applying the composition of claim 24 to the hair, and rinsing the hair with water.

* * * * *